United States Patent
Chou et al.

(10) Patent No.: US 7,326,929 B2
(45) Date of Patent: Feb. 5, 2008

(54) METHOD AND APPARATUS FOR INSPECTION OF SEMICONDUCTOR DEVICES

(75) Inventors: Mau-Song Chou, Rancho Palos Verdes, CA (US); Jonathan W. Arenberg, Santa Monica, CA (US); Mark A. Menard, Chino Hills, CA (US); Thomas T. Chung, Redondo Beach, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 41 days.

(21) Appl. No.: 11/348,029

(22) Filed: Feb. 6, 2006

(65) Prior Publication Data

US 2007/0181809 A1    Aug. 9, 2007

(51) Int. Cl.
    *G02F 1/01*   (2006.01)
(52) U.S. Cl. ................................... 250/330
(58) Field of Classification Search ............... 250/330, 250/331, 332, 333, 334; 438/10, 11, 12, 438/14, FOR. 450
    See application file for complete search history.

(56) References Cited

U.S. PATENT DOCUMENTS

| 4,547,073 A | 10/1985 | Kugimiya |
| 4,794,264 A | 12/1988 | Quackenbos et al. |
| 4,794,265 A | 12/1988 | Quackenbos et al. |
| 5,018,867 A | 5/1991 | Piironen |
| 5,334,844 A | 8/1994 | Pollard et al. |
| 5,640,237 A | 6/1997 | Esrig et al. |
| 5,777,729 A | 7/1998 | Aiyer et al. |
| 5,822,054 A | 10/1998 | Coulthard |
| 6,005,965 A * | 12/1999 | Tsuda et al. ................ 382/145 |
| 6,111,638 A | 8/2000 | Chou et al. |
| 6,236,044 B1 | 5/2001 | Chou et al. |
| 6,420,705 B2 | 7/2002 | Chou et al. |
| 6,433,867 B1 | 8/2002 | Esquivel |
| 6,614,519 B1 | 9/2003 | Latta et al. |
| 6,816,249 B2 | 11/2004 | Fairley et al. |
| 2006/0278831 A1* | 12/2006 | Matsumoto et al. ..... 250/341.1 |

FOREIGN PATENT DOCUMENTS

JP      2004 177320 A      6/2004

OTHER PUBLICATIONS

J.R. Hodor et al., "Optical sensor designs for the detection of cracks in optical materials," SPIE Vo. 1168 Current Devopments in Optical Eng. & Comm. Optics, 138-146 (1989).

(Continued)

*Primary Examiner*—David Porta
*Assistant Examiner*—Mark R Gaworecki
(74) *Attorney, Agent, or Firm*—Carmen B. Patti & Assoc., LLC

(57) ABSTRACT

A technique for providing high-contrast images of defects in semiconductor devices and arrays of such devices, by illuminating each semiconductor device under inspection with broadband infrared radiation, and then forming an image of radiation that is specularly reflected from the semiconductor device. Many semiconductor devices and arrays of such devices have a metal backing layer that specularly reflects the illumination back into an appropriately positioned and aligned camera, selected to be sensitive to infrared wavelengths at which the semiconductor device materials are relatively transparent.

20 Claims, 2 Drawing Sheets

OTHER PUBLICATIONS

J.R. Hodor et al., "Infrared techniques applied to large solar arrays," SPIE vol. 1540 Infrared Technology XVII 331-337 (1991).

A. Scott, "Instrument for the measurement of specular reflectivity of bright metal surfaces," J. Scientific Instruments 37, 435-438 (1960).

* cited by examiner

METHOD AND APPARATUS FOR INSPECTION OF SEMICONDUCTOR DEVICES

BACKGROUND OF THE INVENTION

This invention relates generally to optical thermal imaging techniques and, more particularly, to techniques for detecting defects in semiconductor devices or structures. Semiconductor devices are, of course, widely used in a variety of contexts and are typically fabricated as integrated circuit (IC) chips, or as IC wafers containing large arrays of semiconductor devices. Cracks in a semiconductor device have the potential to severely limit its performance. Once a crack has begun, it is highly probable that it will propagate over time to develop into a more significant crack. Therefore, it is important to detect not only large cracks but also small ones.

Currently, cracks in semiconductor devices are inspected mainly by a thermal method. With an infrared camera, an inspector can see the change in temperature in the device as it is powered up electrically. A "hot" spot may be indicative of the presence of a crack. Typical electrical failures occur when there is temperature rise of over 50° C. By this technique, problems can be detected well in advance of a failure, but such a thermal inspection method can best be used for detection of large cracks, but not for small ones. In addition, a thermal method is an invasive and slow process.

U.S. Pat. No. 6,806,249 describes an optical method for the inspection of a semiconductor wafer using a brightfield and darkfield arrangement. The method appears to be applied mainly to detect the presence of small particles on the surface of a wafer.

Most semiconductor devices and arrays have multiple layers of material that render optical inspection difficult. It will be appreciated, therefore, that there is a need for a method for detection of micro-cracks and other defects that is quick, non-invasive and may be used at the array level as well as the device level. The present invention meets and exceeds these requirements.

SUMMARY OF THE INVENTION

The present invention resides a method and apparatus for detecting defects in semiconductor devices. In method terms, the invention may be defined as a method for detecting defects in at least one semiconductor device or a portion of the device, the method comprising illuminating at least one semiconductor device or a portion of the device with infrared radiation from a flat-panel illuminator oriented to direct the radiation onto the semiconductor device at a selected incident angle; positioning an infrared camera to receive specularly reflected radiation from the at least one semiconductor device or a portion of the device; and forming an image in the camera, representative of radiation specularly reflected from the at least one semiconductor device or a portion of the device, wherein any defects in the at least one semiconductor device are visible in the image as contrasting features.

The illuminating step employs a range of wavelengths, including a band at which the semiconductor device materials are relatively transparent. For example, the illuminator radiates light over a broad band of infrared wavelengths and the camera is sensitive in wavelength range of approximately 1-5 μm or 3-5 μm.

The invention can be used over a wide range of angles of incidence. For example the incident angle of illumination on the semiconductor device under inspection may be in the range of approximately 10° to 30° with respect a normal direction to the semiconductor device.

The method can be used to inspect a single semiconductor device, or an array of such devices.

In terms of apparatus, the invention comprises a flat-panel illuminator, for illuminating at least semiconductor device or a portion of the device with infrared radiation, wherein the flat-panel illuminator is oriented to direct the radiation onto the semiconductor device at a selected incident angle; an infrared camera positioned to receive specularly reflected radiation from the at least one semiconductor device or a portion of the device; and means for forming an image in the camera, representative of radiation specularly reflected from the at least one semiconductor device or a portion of the device. Any defects in the at least one semiconductor device or a portion of the device are visible in the image as contrasting features.

It will be appreciated that the present invention represents a significant advance in the field of semiconductor device inspection techniques. In particular, the invention allows for the inspection of semiconductor devices and arrays in a way that provides high contrast images of any cracks or other defects. Other aspects and advantages of the invention will become apparent from the following more detailed description, taken in conjunction with the accompanying drawings.

DETAILED DESCRIPTION OF THE INVENTION

Figure 1:
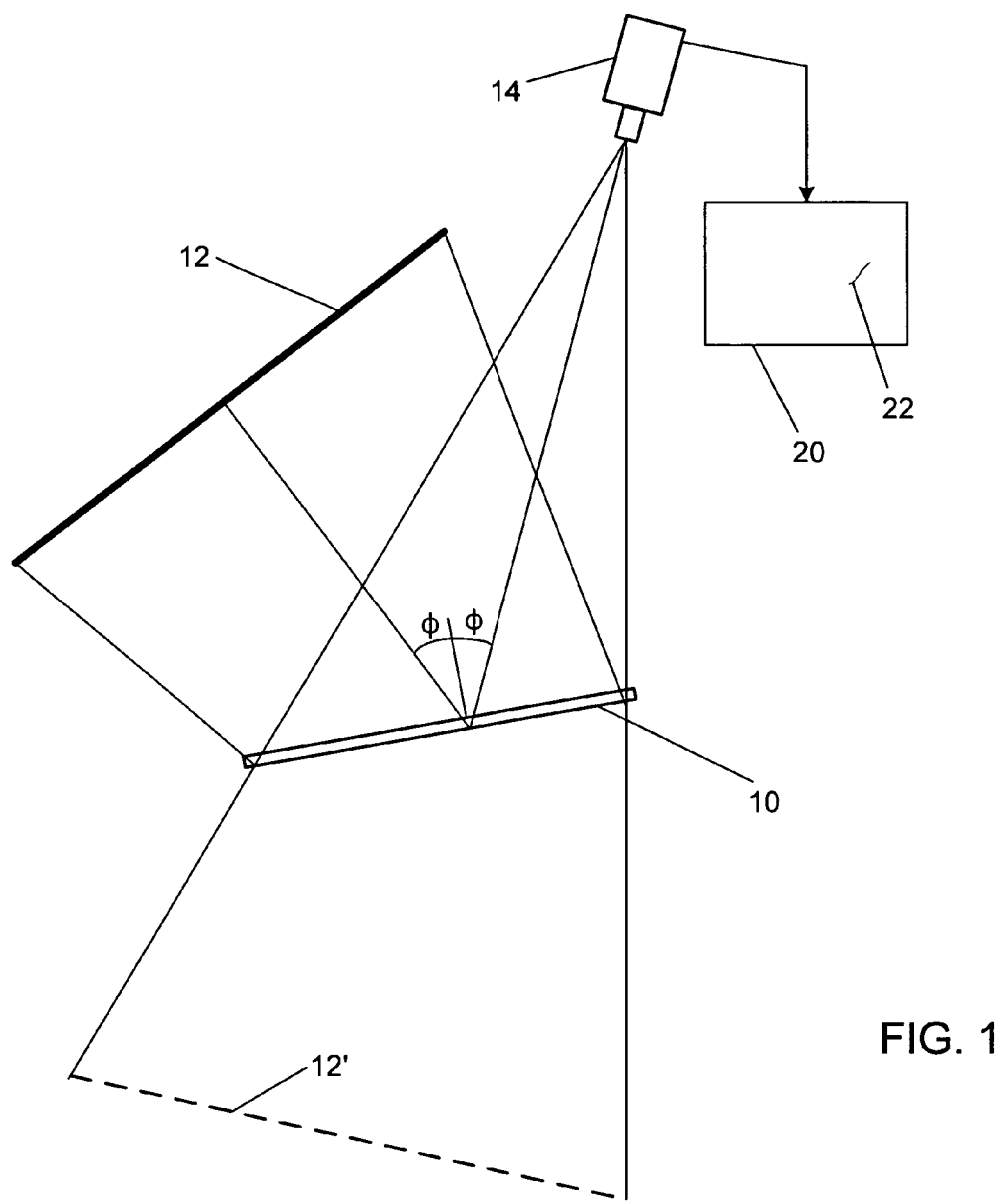
FIG. 1 is a diagram depicting the apparatus of the present invention, including an infrared illuminator and an infrared camera in relation to a semiconductor device under inspection.

As shown in the drawings for purposes of illustration, the present invention is concerned with the detection of defects in semiconductor devices and arrays having reflective back panels. In the past, thermal imaging techniques have been used to locate defects while power is applied to the semiconductor device under inspection. The conventional thermal inspection technique is slow, invasive, and not suitable for semiconductor structures with multiple layers.

In accordance with the present invention, a semiconductor device under inspection, indicated by reference numeral 10, is illuminated with a flat-panel infrared illuminator 12, and then inspected by means of an infrared camera 14 or other imaging device located to record specular reflections from the an underlying reflective layer in the semiconductor device 10. Some semiconductor structures, including photodetector arrays and RF detector arrays, include a metal back plane 16, from which the infrared illumination is specularly reflected. The illuminator 12 is oriented at an angle φ to the semiconductor device 10, so that radiation from the illuminator has an angle of incidence φ with respect to a line drawn normal (perpendicular) to the semiconductor device. Radiation reaching the back plane 16 is specularly reflected in a direction also having an angle φ with respect to the normal direction. The camera 14 is located on and aligned with this line of reflection from the device 10. In effect, the camera 13 sees a mirror image (indicated at 12') of the illuminator 12. The camera 14 produces an image, shown diagrammatically at 20, in which defects, and even micro-cracks, one of which is indicated at 22, are clearly visible. Because the camera image 20 is formed from specularly reflected radiation, i.e., radiation that follows essentially straight-line paths from the illuminator 12 to the device 10 and from the device to the camera 14, any interruption of those straight-line paths, as caused by the presence of a crack, is imaged with diminished brightness in the camera image. Thus the arrangement of the flat-panel illuminator 12 and the camera 14 aligned in the path of specular reflection from the semiconductor device 10, provides a high-contrast image of any defects or cracks encountered by radiation passing through the multiple layers of the semiconductor device. With appropriate sizing and positioning of the flat-panel illuminator 12 and the camera 14, the arrangement can be employed to inspect a broad area of a semiconductor device array comprising multiple arrayed devices.

The camera 14 was selected to provide infrared sensitivity in the range 3-5 microns, although an available 1-5 micron camera also provided good results.

Figure 2:
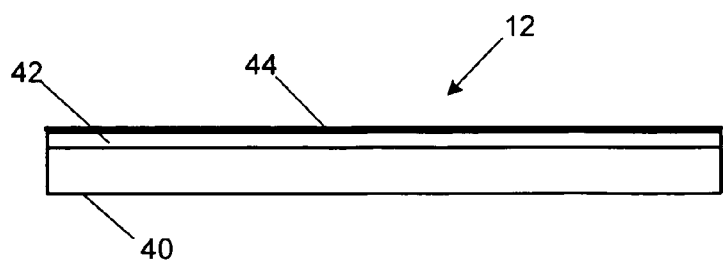
FIG. 2 is a side view of flat-panel infrared illuminator used in the apparatus of FIG. 1.

FIG. 2 shows a little more detail of the illuminator 14. It consists of a commercially available strip heater 40 on which a copper over-layer 42 approximately 0.0625 inch (1.6 mm) thick is installed to provide a more uniform distribution of heat from the strip heater. The copper overlayer 42 is painted with a high-temperature resistant black paint, as indicated at 44 to enhance the uniform radiation properties of the illuminator. The strip heater may be, for example, a mica strip heater from Watlow Electric Manufacturing Company, St. Louis, Mo. The copper plate is attached to the heater surface, by use of a high-temperature thermal conductive epoxy adhesive, to improve the uniformity of temperature of the source. An example of epoxy adhesive is Duralco 133 aluminum-filled epoxy from Contronics, located in Brooklyn, N.Y. As an alternative to painting the copper surface with a flat black paint, the surface can be coated with black chrome. The black paint or the black-chrome coating increases the emissivity and also diffuseness of the illuminator to improve its performance.

Based on the geometric ray traces one can estimate roughly a minimum length (L) of the illuminator required for inspection, as given by:

$$L=2(D1+D2)*X1*\cos \phi/(D1+X1*\sin \phi),$$

where $X1=D1*\cos \phi*(\tan(\phi+\theta)-\tan \phi)$

In these expressions, $\theta$ is half of the subtended angle of the camera 14 to the semiconductor device 10 under inspection. X1 is the portion of the length of the device intercepted by the equal-angle bisector. $\phi$ is the angle of incidence of a central-axis ray from the illuminator 12 onto the semiconductor device 10 and is also the angle of reflection, from the semiconductor device, of the same ray. D1 and D2 are the distance from the device to the camera and the illuminator, respectively. A minimum width of the cell can also be derived based on these equations using the corresponding dimensions. The actual width and length of the illuminator are preferably larger than these minimum values as determined above.

Figure 3:
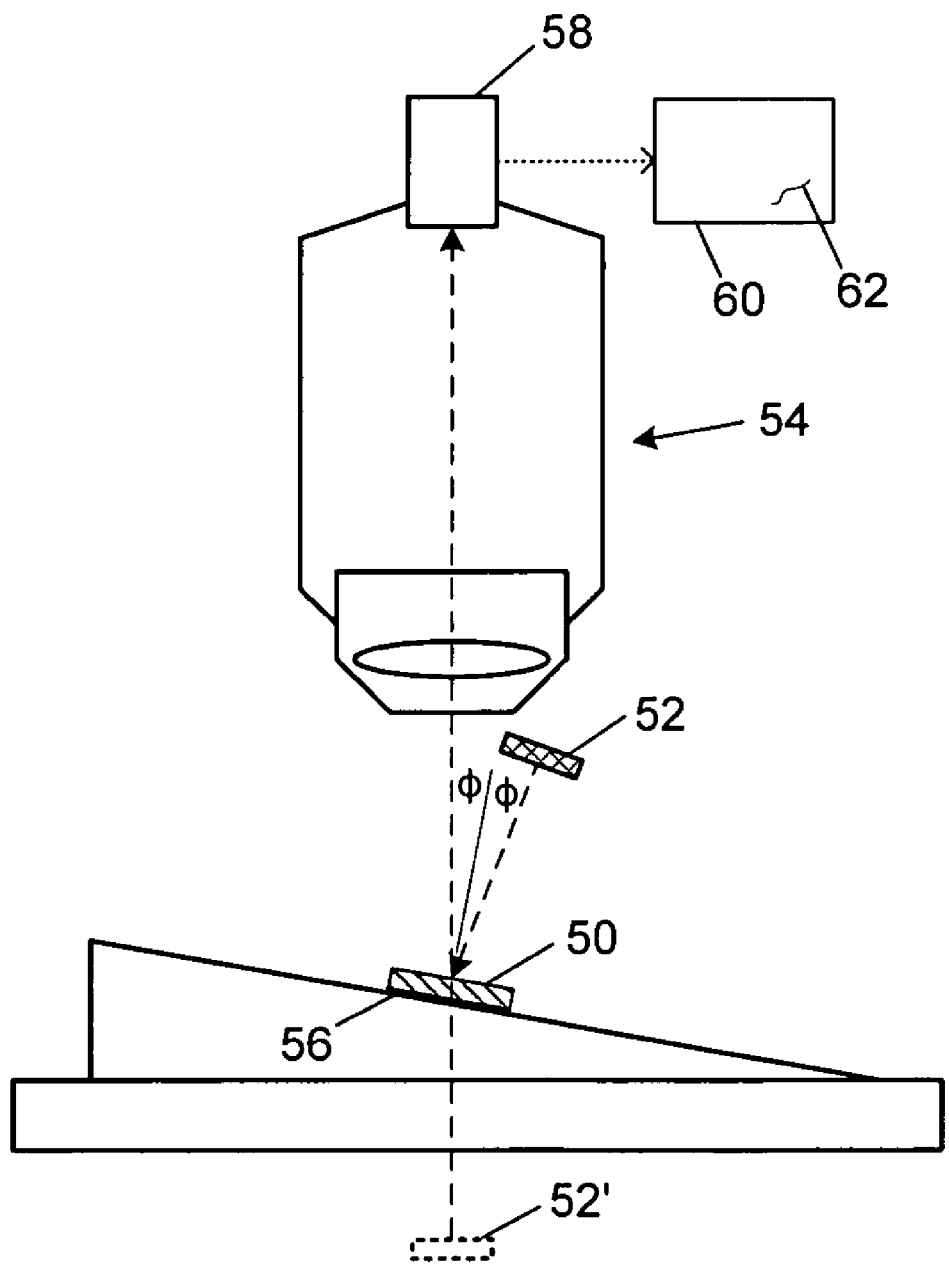
FIG. 3 is a diagram depicting an alternative apparatus of the present invention, including an infrared illuminator and an infrared microscope in relation to a semiconductor device under inspection.

Referring to FIG. 3 for an alternative embodiment of the invention a semiconductor device under inspection, indicated by reference numeral 50, is illuminated with a flat-panel infrared illuminator 52, and then inspected by means of an infrared microscope 54 or other imaging device located to record specular reflections from an underlying reflective layer in the semiconductor device 50. Some semiconductor structures, including photodetector arrays and RF detector arrays, include a metal back plane 56, from which the infrared illumination is specularly reflected. The illuminator 52 is oriented at an angle $\phi$ to the semiconductor device 50, so that radiation from the illuminator has an angle of incidence $\phi$ with respect to a line drawn normal (perpendicular) to the semiconductor device. Radiation reaching the back plane 56 is specularly reflected in a direction also having an angle $\phi$ with respect to the normal direction. The infrared microscope 54 is located on and aligned with this line of reflection from the device 50. In effect, the infrared microscope sees a mirror image (indicated at 52') of the illuminator 52. The infrared microscope 54 includes an infrared camera 58, which produces an image, shown diagrammatically at 60, in which defects, and even microcracks, one of which is indicated at 62, are clearly visible. Because the camera image 60 is formed from specularly reflected radiation, i.e., radiation that follows essentially straight-line paths from the illuminator 52 to the device 50 and from the device to the infrared microscope 54, any interruption of those straight-line paths, as caused by the presence of a crack, is imaged with diminished brightness in the camera image 60. Thus the arrangement of the flat-panel illuminator 52 and the infrared microscope 54 aligned in the path of specular reflection from the semiconductor device 50, provides a high-contrast image of any defects or cracks encountered by radiation passing through the multiple layers of the semiconductor device. With appropriate sizing and positioning of the flat-panel illuminator 52 and the infrared microscope 54, the arrangement can be employed to inspect a broad area of a semiconductor device array comprising multiple arrayed devices.

The infrared microscope 54 was selected to provide infrared sensitivity in the range 3-5 microns, although an available 1-5 micron camera also provided good results. An example of an infrared microscope is Infra Scope II Micro-Thermal Imager, manufactured by Quantum Focus Instrument Corporation, Vista, Calif.

The flat-panel infrared illuminator 52 was selected to provide infrared emission with wavelength 3-5 micron or 1-5 micron. A commercial small-size flat-surface heater, such as a silicone rubber heater or a kapton insulated flexible heater can be conveniently used. The surface temperature is preferably in the range of 50 to 200° C. A thin copper sheet can be attached to the surface of the heater to provide a more uniform temperature distribution across the surface. The surface of the copper sheet (or the bare heater without the copper sheet) can be painted with a high-temperature paint to improve emissivity and diffuseness for source.

It will be appreciated from the foregoing that the present invention provides a significant improvement in the field of inspection of semiconductor devices and arrays for cracks and defects. In particular, the invention allows for the inspection of multi-layer semiconductor structures and provides a high-contrast image in which any cracks are readily discernable. It will also be appreciated that although a specific embodiment of the invention has been described by way of illustration, various modifications may be made without departing from spirit and scope of the invention. Accordingly, the invention should not be limited except as by the appended claims.

The invention claimed is:

1. A method for detecting defects in at least one semiconductor device or a portion of a semiconductor device having a reflective back plane, comprising:

illuminating at least one semiconductor device or a portion of a semiconductor device with infrared radiation from a flat-panel illuminator oriented to direct the radiation onto the semiconductor device at a selected incident angle;

positioning an infrared camera to receive specularly reflected radiation from the at least one semiconductor device or a portion of a semiconductor device; and forming an image in the camera, representative of radiation specularly reflected from the at least one semiconductor device or a portion of a semiconductor device, wherein any defects in the at least one semiconductor device or a portion of a semiconductor device are visible in the image as contrasting features, and wherein the flat-panel illuminator radiates light over a broad band of infrared wavelengths and the camera is sensitive in a wavelength range of approximately 3-5 µm.

2. A method as defined in claim 1, wherein the illuminating step employs a range of wavelengths including a wavelength band at which the semiconductor device materials are relatively transparent.

3. A method as defined in claim 1, wherein the incident angle is in the range of approximately 10° to 30° with respect to a normal direction to the semiconductor device.

4. A method as defined in claim 1, wherein the at least one semiconductor device is part of an array of such devices under simultaneous inspection.

5. Apparatus for detecting defects in at least one semiconductor device or a portion of a semiconductor device, comprising:

a flat-panel illuminator, for illuminating at least one semiconductor device with infrared radiation, wherein the flat-panel illuminator is oriented to direct the radiation onto the semiconductor device at a selected incident angle;

an infrared camera positioned to receive specularly reflected radiation from the at least one semiconductor device or a portion of a semiconductor device; and means for forming an image in the camera, representative of radiation specularly reflected from the at least one semiconductor device or a portion of a semiconductor device, wherein any defects in the at least or a portion of a semiconductor device one semiconductor device are visible in the image as contrasting features, and wherein the flat-panel illuminator radiates light over a broad band of infrared wavelengths and the infrared camera is sensitive in wavelength range of approximately 3-5 µm.

6. Apparatus as defined in claim 5, wherein the flat-panel illuminator employs a range of wavelengths, at least some of which are relatively transparent with respect to the semiconductor material.

7. Apparatus method as defined in claim 5, wherein the incident angle is in the range of approximately 10° to 30° with respect to a normal direction to the semiconductor device.

8. Apparatus as defined in claim 5, wherein the at least one semiconductor device is part of an array of semiconductor devices under simultaneous inspection.

9. A method for detecting defects in at least one semiconductor device or a portion of a semiconductor device having a reflective back plane, comprising:

illuminating at least one semiconductor device or a portion of a semiconductor device with infrared radiation from a flat-panel illuminator oriented to direct the radiation onto the semiconductor device at a selected incident angle;

positioning an infrared microscope to receive specularly reflected radiation from the at least one semiconductor device or a portion of a semiconductor device; and forming an image in the infrared microscope, representative of radiation specularly reflected from the at least one semiconductor device or a portion of a semiconductor device, wherein any defects in the at least one semiconductor device or a portion of a semiconductor device are visible in the image as contrasting features.

10. A method as defined in claim 9, wherein the illuminating step employs a range of wavelengths including a wavelength band at which the semiconductor device materials are relatively transparent.

11. A method as defined in claim 9, wherein the illuminator radiates light over a broad band of infrared wavelengths and the camera is sensitive in wavelength range of approximately 1-5 µm.

12. A method as defined in claim 9, wherein the illuminator radiates light over a broad band of infrared wavelengths and the camera is sensitive in a wavelength range of approximately 3-5 µm.

13. A method as defined in claim 9, wherein the incident angle is in the range of approximately 10° to 30° with respect to a normal direction to the semiconductor device.

14. A method as defined in claim 9, wherein the at least one semiconductor device is part of an array of such devices under simultaneous inspection.

15. Apparatus for detecting defects in at least one semiconductor device or a portion of a semiconductor device, comprising:

a flat-panel illuminator, for illuminating at least one semiconductor device with infrared radiation, wherein the flat-panel illuminator is oriented to direct the radiation onto the semiconductor device at a selected incident angle;

an infrared microscope positioned to receive specularly reflected radiation from the at least one semiconductor device or a portion of a semiconductor device; and means for forming an image in the infrared microscope, representative of radiation specularly reflected from the at least one semiconductor device or a portion of a semiconductor device, wherein any defects in the at least or a portion of a semiconductor device one semiconductor device are visible in the image as contrasting features.

16. Apparatus as defined in claim 15, wherein the flat-panel illuminator employs a range of wavelengths, at least some of which are relatively transparent with respect to the semiconductor material.

17. Apparatus as defined in claim 15, wherein the flat-panel illuminator radiates light over a broad band of infrared wavelengths and the infrared camera is sensitive in a wavelength range of approximately 1-5 µm.

18. Apparatus as defined in claim 15, wherein the flat-panel illuminator radiates light over a broad band of infrared wavelengths and the infrared camera is sensitive in wavelength range of approximately 3-5 µm.

19. Apparatus method as defined in claim 15, wherein the incident angle is in the range of approximately 10° to 30° with respect to a normal direction to the semiconductor device.

20. Apparatus as defined in claim 15, wherein the at least one semiconductor device is part of an array of semiconductor devices under simultaneous inspection.

* * * * *